(12) United States Patent
Yaron et al.

(10) Patent No.: US 6,510,600 B2
(45) Date of Patent: Jan. 28, 2003

(54) METHOD FOR MANUFACTURING A FLOW REGULATING IMPLANT

(75) Inventors: Ira Yaron, Har Adar (IL); Orit Yarden, Givat Shmuel (IL)

(73) Assignee: Optonol, Ltd., Neve Ilan (IL)

(*) Notice: Subject to any disclaimer, the term of this patent is extended or adjusted under 35 U.S.C. 154(b) by 0 days.

(21) Appl. No.: 09/729,050

(22) Filed: Dec. 4, 2000

(65) Prior Publication Data

US 2001/0000527 A1 Apr. 26, 2001

Related U.S. Application Data

(62) Division of application No. 08/975,386, filed on Nov. 20, 1997, now Pat. No. 6,203,513.

(51) Int. Cl.$^7$ ................................................ B23P 11/00
(52) U.S. Cl. ............................ 29/428; 29/445; 604/9; 604/264
(58) Field of Search .................... 29/428, 445, 506, 29/514, 521; 604/93, 264, 8–10, 164, 30, 523

(56) References Cited

U.S. PATENT DOCUMENTS

| | | |
|---|---|---|
| 15,192 A | 6/1856 | Peale |
| 274,447 A | 3/1883 | Kennish |
| 733,152 A | 7/1903 | Chisholm |
| 1,388,172 A | 8/1921 | Craddock |
| 2,431,587 A | 11/1947 | Schnee ........................ 128/348 |
| 2,555,076 A | 5/1951 | Crossley ..................... 128/303 |
| 2,867,213 A | 1/1959 | Thomas, Jr. ................ 128/350 |
| 3,159,161 A | 12/1964 | Ness ........................... 128/350 |
| 3,310,051 A | 3/1967 | Schulte ....................... 128/216 |
| 3,333,588 A | 8/1967 | Schulte ....................... 128/350 |

(List continued on next page.)

FOREIGN PATENT DOCUMENTS

| | | | |
|---|---|---|---|
| EP | 102747 A | | 3/1984 |
| EP | 228185 A | | 7/1987 |
| FR | 2757068 | | 6/1998 |
| JP | 08155540 A | * | 6/1996 |
| SU | 1191227 A | * | 11/1985 |
| WO | WO93/20783 | | 10/1993 |
| WO | WO94/02081 | | 2/1994 |
| WO | WO94/09837 | | 5/1994 |
| WO | WO94/13234 | | 6/1994 |
| WO | WO95/35078 | | 12/1995 |
| WO | WO96/03944 | | 2/1996 |
| WO | WO96/20742 | | 7/1996 |
| WO | WO96/36377 | | 11/1996 |
| WO | WO 98/30181 | | 1/1998 |

Primary Examiner—Gregory M. Vidovich
Assistant Examiner—Jermie E. Cozart
(74) Attorney, Agent, or Firm—Kenyon & Kenyon

(57) ABSTRACT

An implant includes a tube for permitting fluid flow. A flow controlling rod may be inserted within the tube passage. One or more holes around the circumference of the tube may be selectively permanently or temporarily occluded to give desired flow characteristics.

A delivery device for implanting the implant may include a central bore in which a retractable wire is located. The retractable wire penetrates a tube passage of the implant when the implant is attached to the delivery device. A hook on the delivery device prevents the implant from moving down the wire. After the implant is in position in the eye, the retention wire is retracted out of the implant. With the retention wire retracted, the implant is then free to slide away from the hook, allowing the delivery device to be withdrawn, leaving the implant in place.

In a method for manufacturing an implant, two tubes of different diameters are utilized. The smaller tube fits inside the longitudinal bore of the larger tube. When the tubes are cut, the smaller tube forms the tube of the implant and the remaining portions of the larger tube form the retention projection and/or disk of the implant.

16 Claims, 15 Drawing Sheets

U.S. PATENT DOCUMENTS

| | | | |
|---|---|---|---|
| 3,421,509 A | 1/1969 | Fiore .......................... 128/349 |
| 3,530,860 A | 9/1970 | Majoros ..................... 606/109 |
| 3,788,327 A | 1/1974 | Donowitz et al. ...... 128/350 R |
| 3,884,238 A | 5/1975 | O'Malley et al. ........... 128/305 |
| 3,890,976 A | 6/1975 | Bazell et al. ................ 128/351 |
| 3,913,584 A | 10/1975 | Walchle et al. .............. 606/109 |
| 3,915,172 A | 10/1975 | Wichterle et al. ........... 128/350 |
| 3,938,529 A | 2/1976 | Gibbons ..................... 128/349 |
| 3,957,035 A | 5/1976 | Chassaing ................... 128/2 T |
| 3,976,077 A | 8/1976 | Kerfoot, Jr. ................. 128/305 |
| 4,037,604 A | 7/1977 | Newkirk ..................... 128/350 |
| 4,175,563 A | 11/1979 | Arenberg et al. ........ 128/350 V |
| 4,299,227 A | 11/1981 | Lincoff ........................ 128/344 |
| 4,402,681 A | 9/1983 | Haas et al. ..................... 604/9 |
| 4,457,757 A | 7/1984 | Molteno ..................... 604/294 |
| 4,474,569 A | 10/1984 | Newkirk ........................ 604/8 |
| 4,521,210 A | 6/1985 | Wong ............................ 604/8 |
| 4,538,611 A | 9/1985 | Kelman ....................... 128/305 |
| 4,554,918 A | 11/1985 | White .......................... 604/10 |
| 4,563,779 A | 1/1986 | Kelman ........................... 623/5 |
| 4,578,058 A | 3/1986 | Grandon ...................... 604/27 |
| 4,587,954 A | 5/1986 | Haber ........................ 128/1 R |
| 4,598,705 A * | 7/1986 | Lichtenberger ........ 128/200.26 |
| 4,604,087 A | 8/1986 | Joseph ........................... 604/9 |
| 4,634,418 A | 1/1987 | Binder ........................... 604/8 |
| 4,645,493 A | 2/1987 | Ferrando et al. ............. 604/174 |
| 4,692,142 A | 9/1987 | Dignam et al. ................ 604/51 |
| 4,722,724 A | 2/1988 | Schocket ........................ 604/8 |
| 4,750,901 A | 6/1988 | Molteno ........................ 604/8 |
| 4,750,971 A | 6/1988 | Maas et al. |
| 4,751,926 A | 6/1988 | Sasaki ......................... 128/303 |
| 4,781,675 A | 11/1988 | White .......................... 604/10 |
| 4,787,885 A | 11/1988 | Binder ........................... 604/8 |
| 4,808,183 A | 2/1989 | Panje ............................ 623/9 |
| 4,813,941 A | 3/1989 | Shea ........................... 604/247 |
| 4,826,478 A | 5/1989 | Schocket ........................ 604/8 |
| 4,863,457 A | 9/1989 | Lee |
| 4,886,488 A | 12/1989 | White ............................ 604/9 |
| 4,909,783 A | 3/1990 | Morrison ..................... 604/30 |
| 4,934,363 A | 6/1990 | Smith et al. ................. 606/107 |
| 4,936,825 A | 6/1990 | Ugerleider ..................... 604/8 |
| 4,946,436 A | 8/1990 | Smith ............................ 604/8 |
| 4,964,850 A | 10/1990 | Bouton et al. ................ 604/54 |
| 4,968,296 A | 11/1990 | Ritch et al. .................... 604/8 |
| 5,000,731 A | 3/1991 | Wong ............................ 604/8 |
| 5,041,081 A | 8/1991 | Odrich ........................... 604/9 |
| 5,053,040 A | 10/1991 | Goldsmith, III ............ 606/109 |
| 5,064,417 A | 11/1991 | Andreussi ................... 604/175 |
| 5,071,408 A | 12/1991 | Ahmed ....................... 606/108 |
| 5,073,163 A | 12/1991 | Lippman ........................ 604/9 |
| 5,092,837 A | 3/1992 | Ritch et al. .................... 604/8 |
| 5,098,393 A | 3/1992 | Amplatz et al. ............. 604/167 |
| 5,098,438 A | 3/1992 | Siepser ....................... 606/107 |
| 5,106,367 A | 4/1992 | Ureche et al. ................ 604/30 |
| 5,127,901 A | 7/1992 | Odrich ........................... 604/9 |
| 5,139,502 A | 8/1992 | Berg et al. .................. 606/108 |
| 5,147,370 A | 9/1992 | McNamara et al. ........ 606/108 |
| 5,167,620 A | 12/1992 | Ureche et al. ................ 604/28 |
| 5,171,213 A | 12/1992 | Price, Jr. ....................... 604/8 |
| 5,171,270 A | 12/1992 | Herrick |
| 5,178,604 A | 1/1993 | Baerveldt et al. .............. 604/8 |
| 5,190,552 A | 3/1993 | Kelman ...................... 606/107 |
| 5,207,660 A | 5/1993 | Lincoff ....................... 604/300 |
| 5,221,278 A | 6/1993 | Linkwitz et al. ............ 604/890 |
| 5,242,449 A | 9/1993 | Zaleski ....................... 606/107 |
| 5,300,020 A | 4/1994 | L'Esperance, Jr. ............. 604/9 |
| 5,318,558 A | 6/1994 | Linkwitz et al. ............ 604/892 |
| 5,322,504 A | 6/1994 | Doherty et al. ............. 606/167 |
| 5,326,345 A | 7/1994 | Price, Jr. ......................... 623/4 |
| 5,338,291 A | 8/1994 | Speckman et al. ............. 604/9 |
| 5,342,370 A | 8/1994 | Simon et al. ................ 606/107 |
| 5,346,464 A | 9/1994 | Camras ......................... 604/9 |
| 5,358,492 A | 10/1994 | Feibus |
| 5,360,398 A | 11/1994 | Grieshaber et al. ........... 604/30 |
| 5,360,399 A | 11/1994 | Stegmann .................... 604/49 |
| 5,370,607 A | 12/1994 | Memmen ....................... 604/8 |
| 5,372,577 A | 12/1994 | Ungerleider ................... 604/8 |
| 5,380,290 A | 1/1995 | Makower et al. ........... 604/164 |
| D356,867 S | 3/1995 | Krupin ...................... D24/155 |
| 5,397,300 A | 3/1995 | Baerveldt et al. .............. 604/8 |
| 5,403,323 A | 4/1995 | Smith ........................ 606/107 |
| RE34,998 E | 7/1995 | Langerman .................... 623/6 |
| 5,433,701 A | 7/1995 | Rubinstein ..................... 604/8 |
| 5,433,714 A | 7/1995 | Bloomberg ................. 604/289 |
| 5,451,229 A | 9/1995 | Geuder et al. .............. 606/107 |
| 5,454,796 A | 10/1995 | Krupin ....................... 604/294 |
| 5,476,445 A | 12/1995 | Baerveldt et al. .............. 604/8 |
| 5,494,484 A | 2/1996 | Feingold ..................... 606/107 |
| 5,520,631 A | 5/1996 | Nordquist et al. .............. 604/8 |
| 5,522,845 A | 6/1996 | Wenstrom, Jr. ........... 606/78 X |
| 5,558,629 A | 9/1996 | Baerveldt et al. .............. 609/8 |
| 5,558,630 A | 9/1996 | Fisher ........................... 604/8 |
| 5,601,094 A | 2/1997 | Reiss |
| 5,626,558 A | 5/1997 | Suson |
| 5,626,559 A | 5/1997 | Solomon ....................... 604/9 |
| 5,702,414 A | 12/1997 | Richter et al. .............. 606/166 |
| 5,704,907 A | 1/1998 | Nordquist et al. |
| 5,709,698 A * | 1/1998 | Adams et al. ............... 606/180 |
| 5,713,844 A * | 2/1998 | Peyman ......................... 604/9 |
| 5,720,760 A * | 2/1998 | Becker et al. ............... 606/180 |
| 5,800,376 A | 9/1998 | Watson et al. |
| 5,807,240 A * | 9/1998 | Muller et al. ............... 600/135 |
| 5,865,831 A | 2/1999 | Cozean et al. |
| 5,868,697 A | 2/1999 | Richter et al. ................. 604/8 |
| 5,893,837 A | 4/1999 | Eagles et al. |
| 5,968,058 A | 10/1999 | Richter et al. .............. 606/166 |
| 6,004,302 A | 12/1999 | Brierley |
| 6,007,510 A | 12/1999 | Nigam |
| 6,007,511 A | 12/1999 | Prywes |
| 6,050,970 A | 4/2000 | Baerveldt |
| 6,102,045 A | 8/2000 | Nordquist et al. |
| 6,168,575 B1 | 1/2001 | Soltanpour |
| 6,186,974 B1 | 2/2001 | Allan et al. .................. 604/30 |
| 6,203,513 B1 | 3/2001 | Yaron et al. ................... 604/9 |
| 6,221,078 B1 | 4/2001 | Bylsma |
| 6,280,468 B1 | 8/2001 | Schachar |
| 6,299,640 B1 | 10/2001 | Schachar |

\* cited by examiner

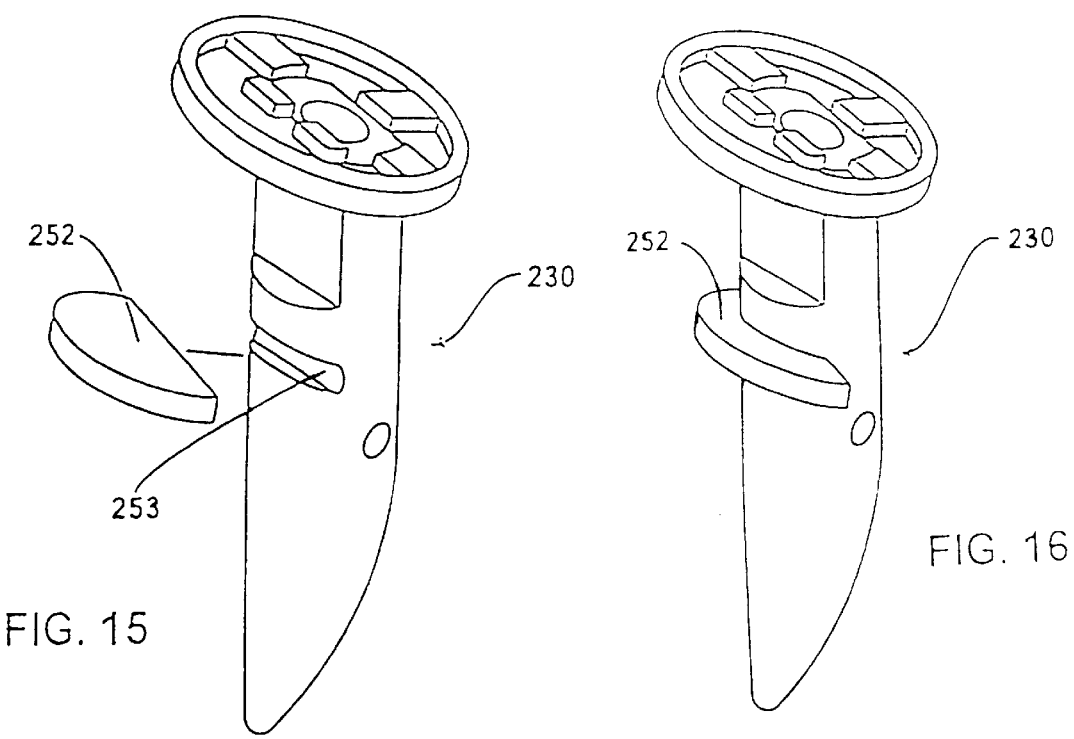

METHOD FOR MANUFACTURING A FLOW REGULATING IMPLANT

This application is a division of prior U.S. patent application Ser. No. 08/975,386, filed Nov. 20, 1997 now U.S. Pat. No. 6,203,513.

FIELD OF THE INVENTION

The invention relates generally to medical implants used to regulate the flow of fluids within the body. The invention may be applied, for example, to ophthalmic implants for treatment of glaucoma. The invention also relates to methods of manufacturing such implants and to delivery devices for implanting such implants.

BACKGROUND OF THE INVENTION

Medical implants used to regulate the flow of fluids within the human body are known and used.

One application for the use of such implants is in the treatment of glaucoma. Glaucoma is an eye condition characterized by an increase in the intraocular pressure (IOP) of the eye to an abnormal level. A normal eye maintains a proper IOP by the circulation within the eye of aqueous humor—aqueous humor is secreted from the ciliary body, passes through the pupil into the anterior chamber of the eyeball, and is filtered out of the eyeball via the trabeculum and the Canal of Schlemm. With glaucoma, the aqueous humor excretory pathway is blocked, the aqueous humor cannot pass out of the eyeball at an adequate rate, the IOP rises, the eyeball becomes harder, and the optic nerve atrophies by the pressure applied on its fibers leaving the retina. A characteristic optic neuropathy develops, resulting in progressive death of the ganglion cells in the retina, restriction of the visual field, and eventual blindness. Advanced stages of the disease are characterized also by significant pain.

Glaucoma treatment, if initiated early in the course of the disease, can prevent further deterioration and preserve most of the ocular functions. The goal of glaucoma treatment is to reduce the IOP to a level which is considered safe for a particular eye, but which is not so low as to cause ocular malfunction or retinal complications.

One type of glaucoma treatment is filtration surgery, which provides an alternate route for aqueous humor to exit the anterior chamber of the eyeball and enter the sub-conjunctival space, thereby lowering the IOP. In full thickness operations a fistula is created through the limbal sclera, connecting directly the anterior chamber of the eyeball and the sub-conjunctival space. Full thickness operations provide long-lasting control of IOP; however, excessive loss of aqueous humor from the eyeball during the early postoperative period frequently leads to hypotony.

In guarded filtration surgery (trabeculectomy), a fistula created through the limbal sclera is protected by an overlying partial thickness sutured scleral flap. The scleral flap provides additional resistance to excessive loss of aqueous humor from the eyeball, thereby reducing the risk of early postoperative hypotony. However, trabeculectomy may result in higher eventual IOP and increased risk of late failure of filtration, compared with full thickness operations.

In accordance with one recently introduced procedure, a full thickness filtering fistula may be created by a holmium laser probe, with minimal surgically induced trauma. After retrobulbar anesthesia, a conjunctival incision (approximately 1 mm) is made about 12–15 mm posterior to the intended sclerostomy site, and a laser probe is advanced through the sub-conjunctival space to the limbus. Then, multiple laser pulses are applied until a full thickness fistula is created. This technique has sometimes resulted in early hypotony on account of a difficulty in controlling the sclerostomy size. In addition, early and late iris prolapse into the sclerostomy has resulted in abrupt closure of the fistula and eventual surgical failure. Further, despite its relative simplicity, the technique still necessitates the use of retrobulbar anesthesia to avoid pain caused by the laser applications. The injection of anesthetic material close to the already damaged optic nerve may sometimes lead to further visual damage. A further disadvantage of this procedure, as well as other types of glaucoma filtration surgery, is the propensity of the fistula to be sealed by scarring.

Various attempts have been made to overcome the problems of filtration surgery, for example, by using ophthalmic implant devices. Typical ophthalmic implants utilize drainage tubes so as to maintain the integrity of the openings formed in the eyeball for the relief of the IOP.

Typical ophthalmic implants suffer from several disadvantages. For example, the implants typically utilize a valve mechanism for regulating the flow of aqueous humor from the eyeball; defects in and/or failure of such valve mechanisms could lead to excessive loss of aqueous humor from the eyeball and possible hypotony. The implants also tend to clog over time, either from the inside by tissue, such as the iris, being sucked into the inlet, or from the outside by the proliferation of cells, for example by scarring. Additionally, the typical implant insertion operation is complicated, costly and takes a long time.

U.S. Pat. No. 3,788,327 to Donowitz et al. shows a prior art implant utilizing a valve mechanism for regulating the flow of aqueous humor from the eyeball. As stated above, defects in and/or failure of such a valve mechanism could lead to excessive loss of aqueous humor from the eyeball and possible hypotony. Additionally, both the inlet opening and the outlet opening in the implant shown in U.S. Pat. No. 3,788,327 may be susceptible to clogging—the inlet opening by the iris and the outlet opening by scarring. Finally, implantation of an implant according to U.S. Pat. No. 3,788,327 may involve the separate steps of first providing a tract for receiving the. implant and/or suturing the implant once it is in place, which add time and possible complications to the operation.

SUMMARY OF THE INVENTION

It is an object of the invention to provide an improved implant to regulate the flow of fluids within the body. The invention may be applied, for example, to an ophthalmic implant which may be implanted into the eyeball for the treatment of glaucoma. It is a further object of the invention to provide a method of manufacturing such an implant and a delivery device for implanting such an implant.

In one embodiment of an improved implant in accordance with the invention, an intraocular implant is provided to be implanted in the eyeball. The implant includes a tube having an inlet end, an outlet end, and a tube passage therebetween for permitting aqueous humor to flow out of the eyeball, and a disk connected to the tube at the outlet end of the tube. The tube passage may have a cross-sectional area sufficiently small to inhibit the flow of aqueous humor through the tube passage. A flow controlling wire or rod may be inserted within the tube passage to provide further control over the flow. The configuration of the flow controlling rod may be selected in accordance with the desired flow characteristics.

The configuration may be chosen to prevent flow when the IOP is below a threshold amount.

The disk, which is designed to be located underneath the conjunctiva, may have an outer rim for forming a reservoir having an enlarged cross-sectional area relative to the cross-sectional area of the tube passage. When aqueous humor flows through the tube passage, a bleb of aqueous humor forms under the conjunctiva so that the bleb and the elasticity of the conjunctiva assist in regulating the flow of aqueous humor through the tube as a function of the IOP.

To prevent clogging of the implant, the tube at its inlet end may be provided with a beveled surface which faces away from the iris when the implant is inserted. Additionally, one or more circumferential holes may be provided along the tube for allowing aqueous humor to flow into the tube passage even if the axial inlet opening is blocked. The hole or holes may be selectively permanently or temporarily occluded to give desired flow characteristics.

To prevent clogging at the outlet end, the disk may have an outer rim as described above which raises the conjunctiva away from the axial outlet of the tube passage to allow outflow. One or more inner uprights (which may be in the form of an inner rim) may also be provided on the disk for this purpose. Clogging is further avoided by implanting the implant under the conjunctiva at a distance away from an insertion slit in the conjunctiva, such that healing of the slit does not cause scar tissue to form in the area of the axial outlet opening of the implant.

Implantation may be facilitated by further features of the implant. For example, the implant may have one or more retention projections (for example, in the form of a spur, flange, or plate). The retention projection may be rigid, or it may be made of an elastic material such that it is able to be flexed inward against the tube during penetration through the sclera. Alternatively, the retention projection may be designed to lie initially relatively flat against the tube for easier penetration through the sclera and to prevent tearing of the sclera, with a mechanism for extending the retention projection outwardly when the implant is implanted in the eyeball. For example, the retention projection may be extended outwardly by a separate expansion tool or may be constructed of a shape memory material, such as PMMA or nitinol, so that it is extended outwardly when subjected to the heat of the eyeball. One or more such retention projections are sufficient to reliably anchor the implant in the eyeball without the need for sutures, saving time and costs.

Implantation may also be facilitated by the provision of one or more markers on the implant visible through the cornea upon passing through the sclera. For example, a circumferential hole as described above may serve as a marker; alternatively, the marker may be some other suitable visible mechanism, such as a scratch or colored mark on the tube. The visibility of the marker lets the doctor know that the marker has passed through the sclera, indicating that the implant is in place.

Implantation of an implant may be performed by use of a delivery device comprising a handle and a rodlike instrument, for example a needle or probe, for carrying the implant for insertion. The delivery device has a tip for insertion into the tube passage of the implant and a suitable retention mechanism for preventing the implant from moving up the delivery device during implantation. The retention mechanism may also be constructed to prevent the implant from rotating during implantation to insure proper orientation of the implant. The delivery device may additionally have a suitable expansion tool for extending one or more retention projections of the implant outwardly once the projection or projections have penetrated through the desired tissue.

In an embodiment of a delivery device according to the invention, the rodlike instrument has a central bore in which is located a retractable wire. The retractable wire penetrates a tube passage of the implant when the implant is attached to the delivery device. A hook on the delivery device prevents the implant from moving down the wire. After the implant is in position in the desired implantation site, the retention wire is retracted out of the implant. With the retention wire retracted, the implant is then free to slide away from the hook, allowing the delivery device to be withdrawn, leaving the implant in place.

In one method of implanting an implant according to the invention, a small slit is cut in a portion of the conjunctiva which normally lies at a distance away from the intended implantation site. As the implant itself is very small, the slit also may be very small, for example about 2 mm in length or less. The small size of the slit as well as its positioning at a distance away from the implantation site, for example about 10 mm, helps prevent contamination of the sclerostomy site and reduces the risk of infection.

The implant is placed through the slit, directed to the implantation site, and inserted into the sclera at the implantation site. The sclera may be pierced either by a needle-like tip of the tube of the implant formed by a beveled surface at the inlet end of the tube as described above or by the tip of a needle of the delivery device which carries the implant. Thus, the implant may be inserted directly into the eyeball without the need for any separate piercing step, resulting in cost and time savings.

In a method for manufacturing an intraocular implant according to the invention, two tubes of different diameters are utilized. The smaller tube is able to fit inside the longitudinal bore of the larger tube. When the tubes are cut, the smaller tube forms the tube of the implant and the remaining portions of the larger tube form the retention projection and disk of the implant.

An intraocular implant according to the invention provide the advantages of a full thickness fistula, while avoiding the limitations of the standard trabeculectomy. An implant according to the invention may be very small and implantable without surgery. No surgery room or hospitalization is necessary, thereby reducing costs. Implantation is minimally invasive, simple and quick, requiring only local anesthesia. Retrobulbar anaesthesia is not necessary, and thus iatrogenic damage to the optic nerve is avoided. There is no need to perform an iridectomy, and thus aqueous flow is maintained, lens nourishment is unaffected, and the likelihood of cataracts developing as a result of the procedure is reduced.

An implant according to the invention has other applications aside from the field of intraocular implants. For example, the implant may be used for drainage of a hydrocele sac, regulating flow between the hydrocele sac and the subcutaneous scrotum. As will be appreciated by persons of ordinary skill in the art, other applications of an implant in accordance with the invention are possible.

BRIEF DESCRIPTION OF THE DRAWINGS

FIGS. 15 and 16 illustrate a third embodiment of an intraocular implant with FIG. 15 showing the implant prior to attachment of a retention plate and FIG. 16 showing the implant after attachment of the retention plate;

DETAILED DESCRIPTION OF THE DRAWINGS

Figure 1:
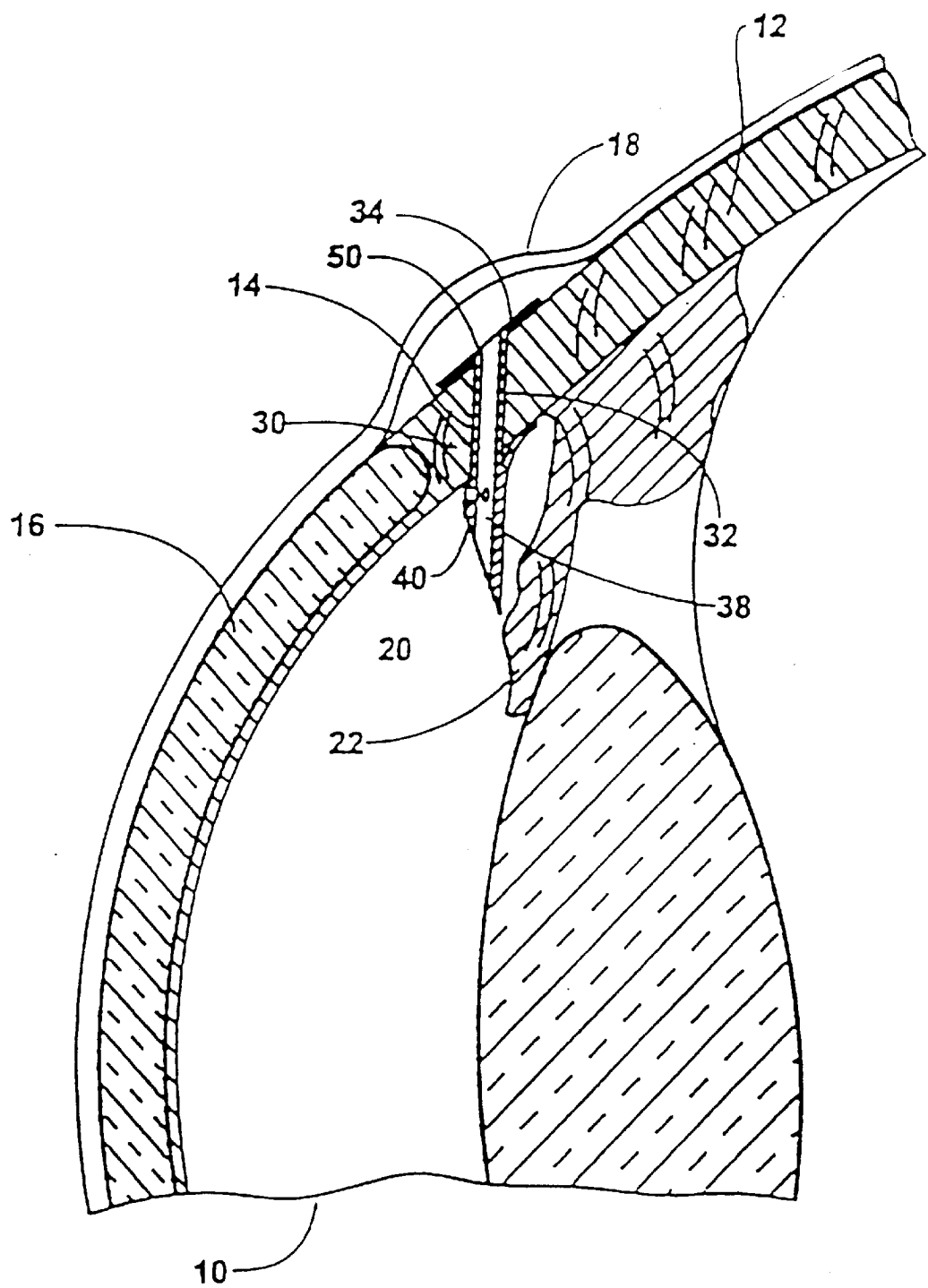
FIG. 1 is a schematic cross-sectional view of a first embodiment of an intraocular implant shown inserted in an eyeball.

FIG. 1 illustrates an intraocular implant 30, implanted in an eyeball 10. The implant 30 comprises a needle-like tube 32 and a disk 34. The plane of the disk 34 forms an angle with the tube 32 that corresponds to the angle between the surface of the sclera 12 and the axis of insertion of the implant 30. The implant 30 is inserted in the sclera 12 of the eyeball 10, in the limbal area 14 adjacent to the cornea 16, and protrudes into the anterior chamber 20 adjacent the iris 22. The implant 30 is inserted so that the disk 34 is placed on a surface of the sclera 12 underneath the conjunctiva 18. The implant 30 may be placed above or below the Tenon's capsule (not shown). It will be appreciated by persons of ordinary skill in the art that the exact location for inserting the implant 30 is not restricted to that shown, and may be any other suitable position, such as behind the iris 22.

Figure 2:
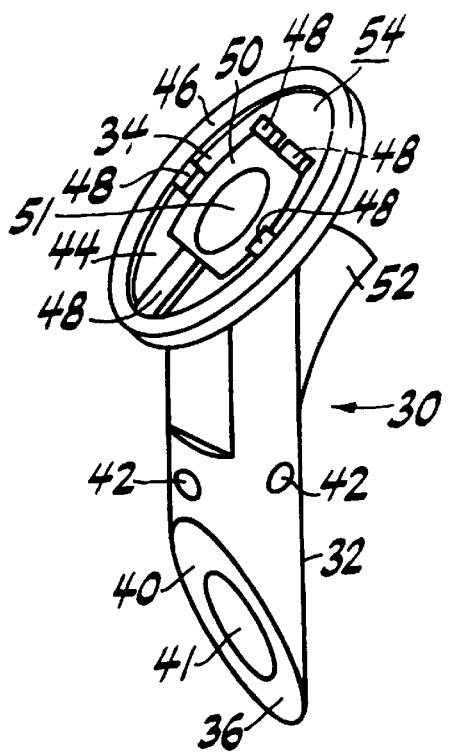
FIG. 2 is an enlarged perspective view of the intraocular implant of FIG. 1.
Figure 3:
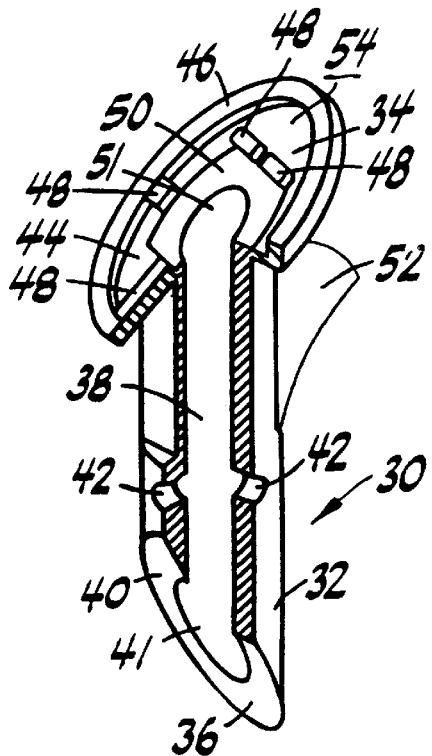
FIG. 3 is a view similar to FIG. 2, with part of the intraocular implant cut away to show a sectional view thereof.

FIG. 2 shows an enlarged perspective view of the implant 30 of FIG. 1, and FIG. 3 shows a similar view, with part of the implant 30 cut away. The tube 32, which may take the form of a modified standard retrobulbar tip, has an inlet end 40, an outlet end 50, and a tube passage 38 extending therebetween, with the tube passage 38 having an axial inlet 41 and an axial outlet 51. The disk 34 is connected to the tube 32 at its outlet end 50. The entire implant is very small; for example the tube 32 may have a length of about 2 mm and a width of about 0.5 mm, and the disk 34 may have a diameter of about 1 mm and a thickness of less than 0.1 mm.

The tube passage 38 has a cross-sectional area sufficiently small to inhibit the flow of aqueous humor through the tube passage. In one embodiment, for example, the cylindrical tube passage 38 has a diameter of about 300 micrometers. By using a specified internal cross-sectional area for the tube passage, excessive loss of aqueous humor from the eyeball is prevented.

When the IOP is above a threshold amount, for example about 5 mm Hg, aqueous humor drains from the anterior chamber 20 of the eyeball 10 through the axial inlet 41 and one or more circumferential holes 42, through the tube passage 38, and into the space under the conjunctiva 18. The circumferential holes 42 may take any suitable form; for example, they may be in the form of circular openings whose combined cross-sectional area is equal to the cross-sectional area of the tube passage 38. The circumferential holes 42 prevent the tube passage 38 from becoming clogged at its inlet end because, even if the iris 22 obstructs the axial inlet 41, aqueous humor can still pass through the circumferential holes 42. In the event the axial inlet 41 is obstructed, the circumferential holes 42 also serve to cause a back pressure in the tube passage 38 to unclog the axial inlet 41. The circumferential holes 42 serve the additional purpose of insuring a proper insertion depth of the implant 30, as the upper hole is visible during implantation after penetration through the sclera and thus can be used as a marker. To serve this function, any other suitable marker (such as a scratch or colored mark) may be used.

The inlet end 40 of the tube 32 has a needle-like tip formed by a beveled surface 36, angled sharply for easy insertion into the eyeball. The beveled surface 36 increases the area of the axial inlet 41 to enlarge the entrance to the tube passage 38. The beveled surface 36 is designed to face away from the iris 22 to reduce the possibility of obstruction of the axial inlet 41. Because the disk 34 is designed to rest against the sclera 12 and the beveled surface 36 is designed to face away from the iris 22, the beveled surface 36 lies in a plane which is angled opposite to the plane in which the disk 34 lies.

The tube 32 may have one or more retention projections in the form of one or more spurs 52 provided integrally with it for retaining the implant 30 in the eyeball 10 after insertion. Alternatively, the retention spur 52 may be made as a separate part connected to the tube 32 by, for example, welding or brazing. The retention spur 52 may be rigid, or it may be flexible such that it bends toward the tube 32 during penetration of the sclera and springs outward to its original shape after passing through the sclera. Alternatively, the retention spur 52 may be designed for plastic deformation by a separate expansion tool (for example, a balloon) once it is in the eyeball 10, or the retention spur 52 may be constructed of a shape memory material, such as PMMA or nitinol, such that the spur is flat against the tube when cool but expands to its final shape when subjected to the heat of the eyeball 10.

Figure 4:
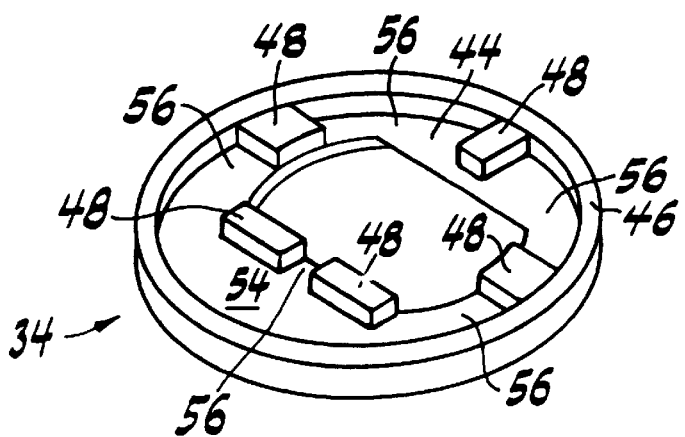
FIG. 4 is an enlarged perspective view of a disk portion of the intraocular implant of FIG. 1.

The disk 34, shown enlarged in FIG. 4, comprises a base 44, an outer rim 46, and a plurality of inner uprights 48. The areas between the uprights 48 constitute passageways 56 for the transverse flow of aqueous humor. The base 44 and outer rim 46 define a reservoir 54 such that, in operation, the aqueous humor flows out of the axial outlet 51 of the tube passage 38, between the uprights 48, and into the reservoir 54. The passageways 56 may be considered as part of the reservoir 54. The enlarged cross-sectional area of the reservoir 54 as compared to the cross-sectional area of the tube passage 38 provides a larger area for absorption of the aqueous humor by the conjunctiva 18 and also acts in conjunction with the elasticity of the conjunctiva 18 to assist in regulating the flow of aqueous humor through the implant 30 as a function of the IOP.

Figure 5:
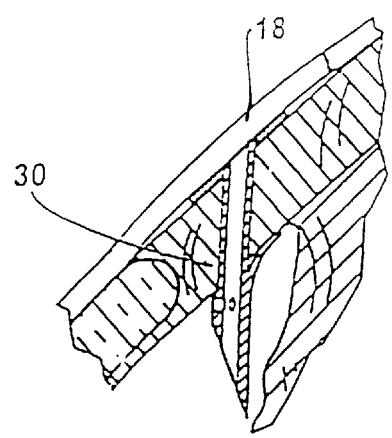
FIGS. 5 through 7 illustrate the action of the conjunctiva during operation of the intraocular implant of FIG. 1, with FIG. 5 showing a stage of operation without a bleb formed, FIG. 6 showing a formation of the bleb, and FIG. 7 showing further formation of the bleb.
Figure 6:
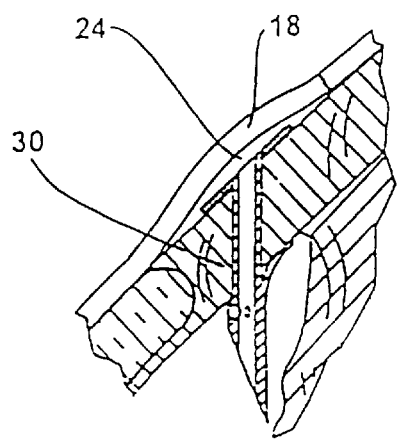
Figure 7:
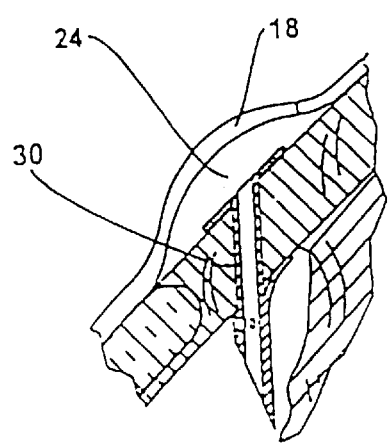

FIGS. 5 through 7 illustrate the action of the conjunctiva 18 during operation of the implant 30, in which it can be seen that the aqueous humor which flows out of the tube passage forms a "bleb" 24 below the conjunctiva 18. It will be appreciated by persons having ordinary skill in the art that a higher IOP results in a higher flow rate through the implant 30, and a greater force of the aqueous humor on the conjunctiva 18.

In addition to defining the reservoir 54, the outer rim 46 of the disk 34 serves the additional purpose of raising the conjunctiva 18 away from the axial outlet 51 to prevent clogging of the tube passage 38. The inner uprights 48 also serve this purpose.

The shape of the disk 34 may be, but is not limited to, an ellipse, and it will be appreciated by persons having ordinary skill in the art that it may conform to any shape which allows the implant to fit under the conjunctiva 18 and which regulates the IOP. The size and/or shape of the disk 34 and/or the angle between the disk 34 and the tube 32 can also be changed in order to use different implants for different persons' eyes.

Figure 8:
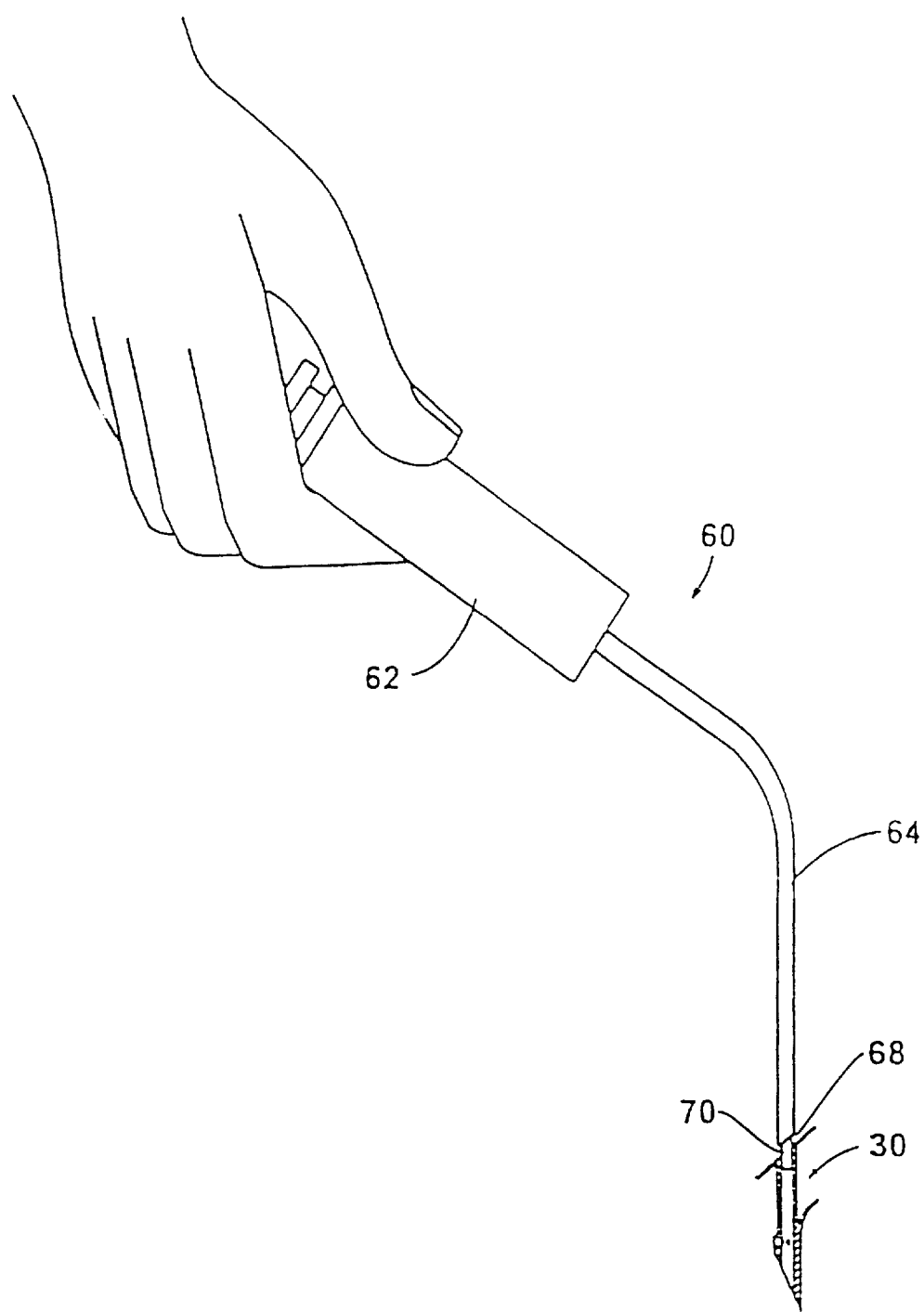
FIGS. 8 through 10 illustrate a delivery device and insertion of the intraocular implant of FIG. 1 into an eyeball, with FIG. 8 showing the delivery device and implant before insertion, FIG. 9 showing the delivery device and implant being placed through a slit in the conjunctiva, and FIG. 10 showing the implant after insertion with the delivery device withdrawn.
Figure 9:
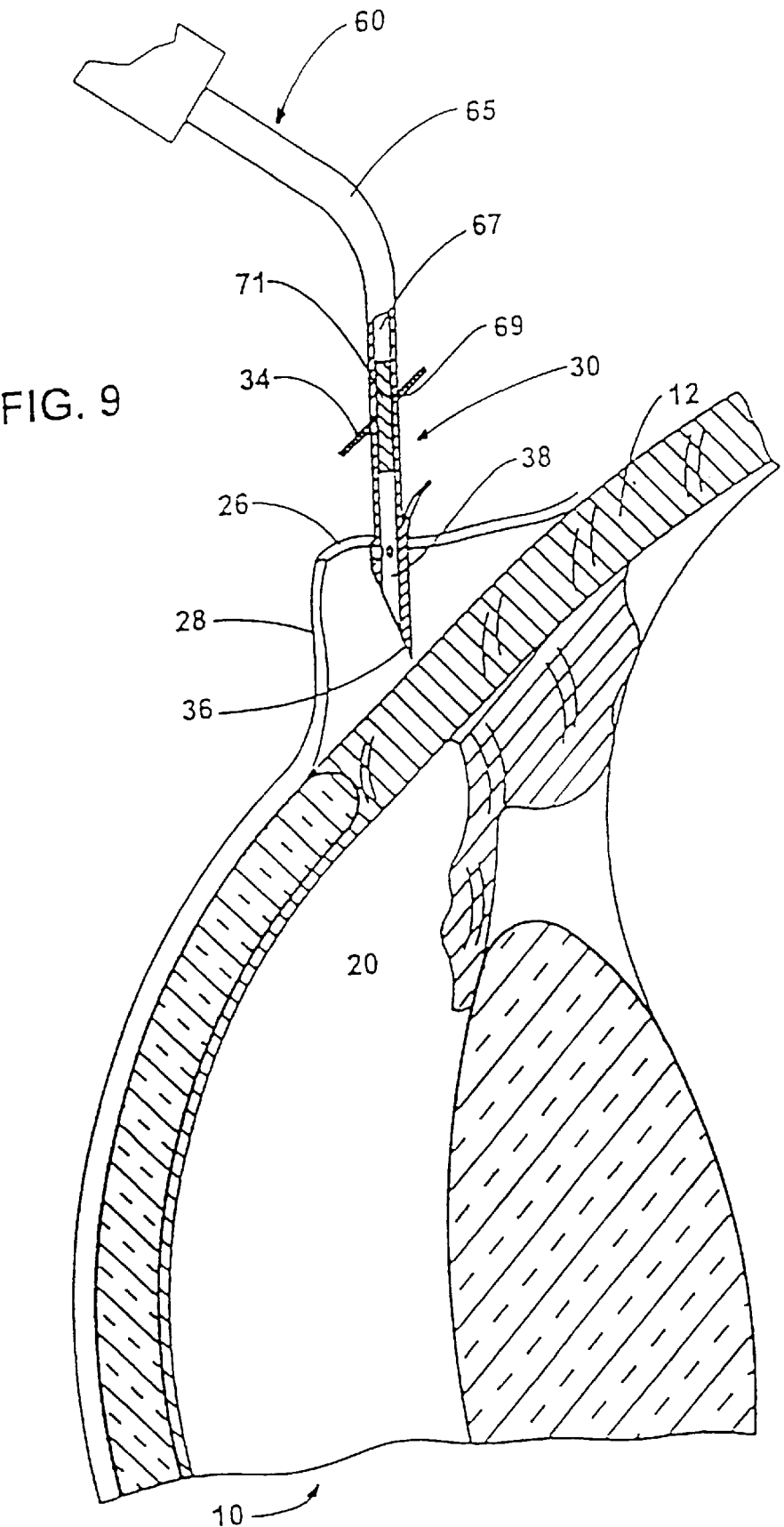
Figure 10:
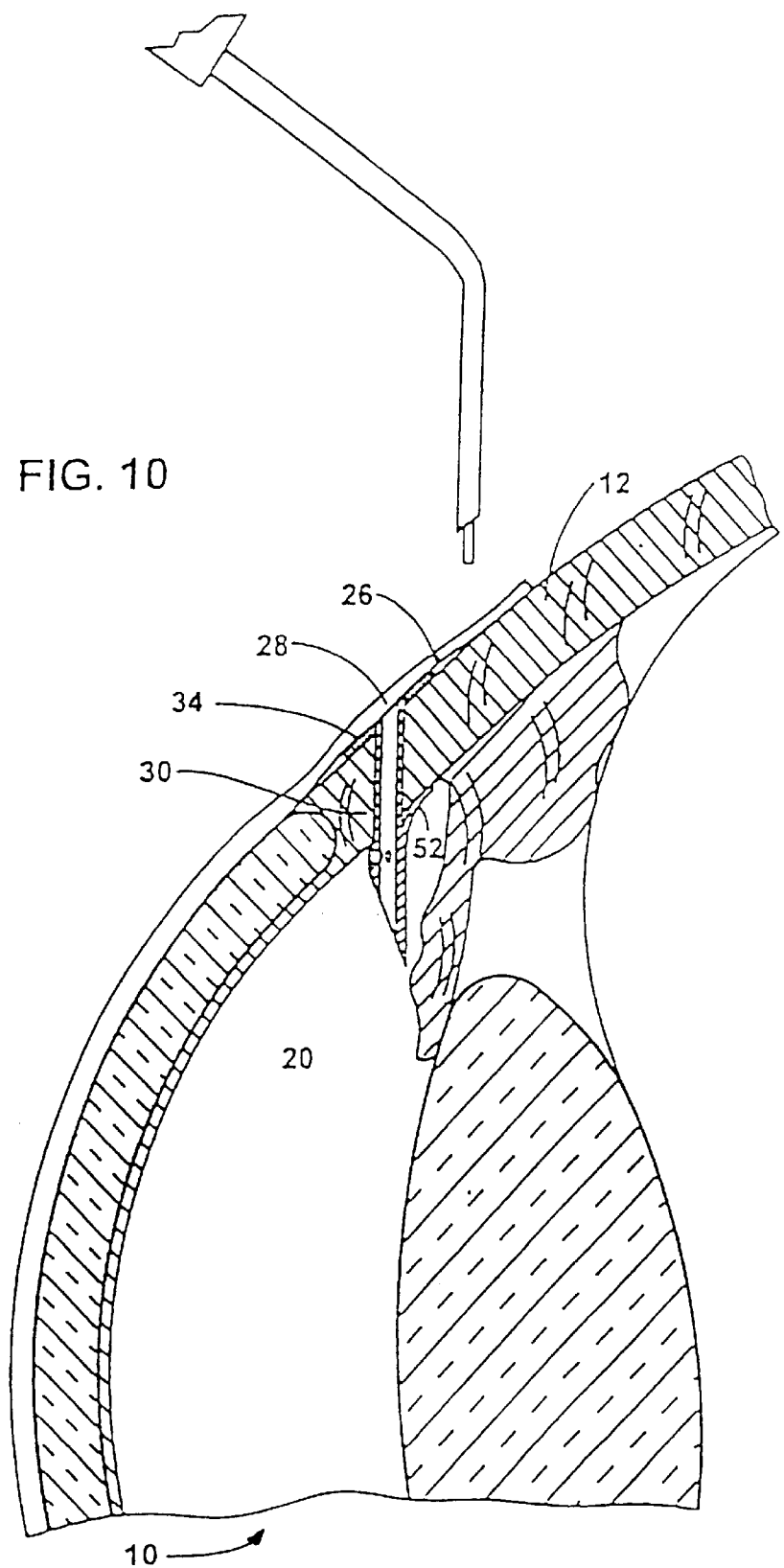

FIGS. 8 through 10 illustrate a delivery device 60 and a method of inserting the intraocular implant 30 into an eyeball. The implant 3.0 is first attached to the delivery device 60, having a handle 62 and a suitable rodlike instrument 64 such as a needle or probe. The rodlike instrument 64 has a tip 70 for penetrating a tube passage of the implant 30 and a retention mechanism for preventing the implant from moving up the delivery device during implantation, for example in the form of an abutment surface 68 having an angle generally corresponding to that of the disk 34. This configuration also prevents rotation of the implant 30 on the delivery device 60, thereby insuring proper orientation of the implant in the eyeball. The retention mechanism may also include one or more projections for extending inside the outer rim and/or between the inner uprights on the disk 34. In an alternative embodiment, the retention mechanism may be the tip of the rodlike instrument, constructed to engage the inside of the tube passage of the implant with a friction fit, thereby preventing the implant from moving up the delivery device during implantation.

A delivery device 60 in which the rodlike instrument is a needle 65 is illustrated in FIG. 9. In that illustrated embodiment, the delivery device 60 is similar to a standard medical syringe having a housing and a needle 65 with a bore 67. The front tip 69 of the needle 65 is configured as an abutment surface having an angle generally corresponding to that of the disk 34. The bore 67 of the needle 65 has a tip in the form of a plug 71 which is configured to have a cross-sectional shape corresponding to that of the tube passage 38. The implant 30 is placed over the plug 71, with the end of the plug 71 projecting into the tube passage 38, and with the front tip 69 of the needle 65 abutting against the disk 34. The plug 71 blocks the tube passage 38 during implantation.

To insert the implant 30 into the eyeball 10, a small slit 26 is cut in a portion of the conjunctiva 18 which normally lies at a distance away from a portion 28 of the conjunctiva 18 which normally covers the intended implantation site. A small slit distanced away from the implantation site, for example a 1–2 mm slit about 5–15 mm away from the implantation site, reduces the possibility of aqueous humor flowing out of the conjunctiva through the slit, reduces the possibility of infection, reduces the possibility of scarring over the axial outlet of the implant, and facilitates closing and healing.

The implant 30, by delivery device 60, is passed through the slit 26, under the conjunctiva 18, to the implantation site in the sclera 12. FIG. 9 shows the advancement of the implant only schematically; it will be appreciated that in practice, the implant is directed from the slit to the implantation site generally along the surface of the sclera, such that the longitudinal axis of the implant is generally parallel to the surface of the sclera. Upon reaching the implantation site, the implant is tilted for penetration into the sclera. The acute angle of the needle-like tip formed by the beveled surface 36 of the implant 30 ensures that the implant 30 enters the sclera 12 easily. The needle-like tip penetrates through the sclera 12 into the anterior chamber 20 of the eyeball 10, while the disk 34 is pushed up against the sclera 12.

When the implant 30 is in place, as shown in FIG. 10, the retention spur (or spurs) 52 anchors the implant 30 in the eyeball 10 and prevents the implant 30 from sliding out as the delivery device 60 is withdrawn. The retention spur 52 also prevents the implant 30 from slipping out once in place.

It will be appreciated by persons having ordinary skill in the art that the insertion of the implant is not restricted to the method described above, and it may be inserted by any of several methods known in the art. The delivery device may comprise an 'internal' or 'external' needle. A straight or twisted guide wire, known in the art, may also be used to guide the delivery device to its precise position. To ease insertion, the delivery device may be vibrated, or a lubricant, such as medical paste or gel, can be spread onto the delivery device. Additionally, after implantation of the implant a suitable fibrosis inhibiting compound (e.g. 5FU, mitomycin) may be applied to the implantation site.

Figure 11:
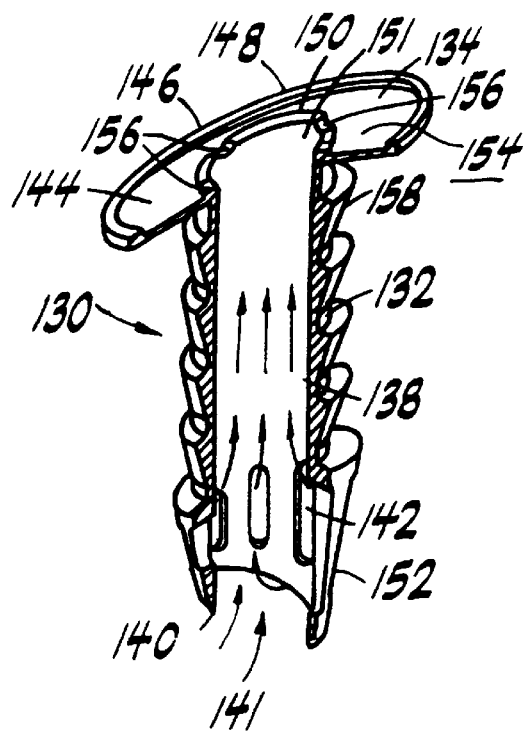
FIG. 11 is an enlarged perspective view of a second embodiment of an intraocular implant with part of the intraocular implant cut away to show a sectional view thereof.

FIG. 11 shows an alternative embodiment of an intraocular implant 130. The implant 130 comprises a tube 132 attached to an elliptical disk 134. The tube 132 has an inlet end 140, an outlet end 150, and a tube passage 138, with the tube passage 138 having an axial inlet 141, an axial outlet 151, and circumferential holes 142 to drain the aqueous humor from the anterior chamber 20 of the eyeball 10 into the space under the conjunctiva 18.

The distal end 152 of the tube 132 has a partially conical shape. A plurality of retention projections in the form of retention flanges 158 are formed on the outer circumference of the tube 132, approximately parallel to the disk 134, to act as anchors to retain the implant 130 in the eyeball.

Figure 12:
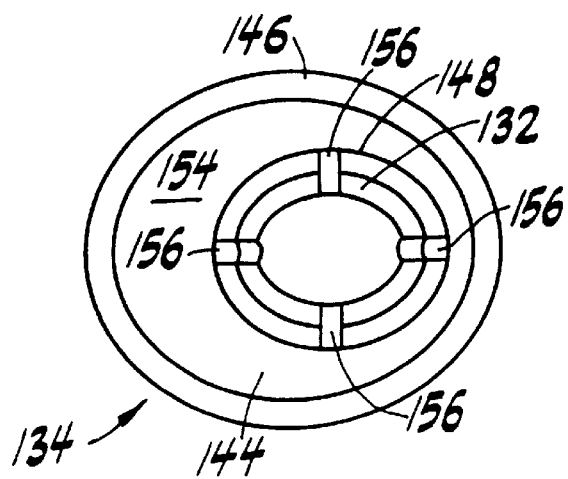
FIG. 12 is a top view of the intraocular implant of FIG. 11, showing a disk portion of the implant.

As shown in the enlarged view in FIG. 12, the disk 134 comprises an elliptical base 144, an outer rim 146, and an inner upright curved to form an inner rim 148, defining therebetween a reservoir 154. A plurality of "U"-shaped passageways 156 are formed in the inner rim 148 for allowing aqueous humor to flow from the axial outlet 151 into the reservoir 154. The outer rim 146 and the inner rim 148 prevent the conjunctiva 18 from clogging the axial outlet 151.

As shown in FIG. 12, the disk 134 is elliptical in shape. The longer axis of the disk 134 is approximately twice the diameter of the tube 132, and the disk 134 is eccentrically displaced relative to the tube 132. The elliptical shape and placement of the disk 134 allows a wide anchoring area for the implant 130 and maximizes the outlet drainage area on the longer axis of the ellipse. The shorter axis of the ellipse enables the implant 130 to fit within the narrow space under the conjunctiva 18.

Figure 13:
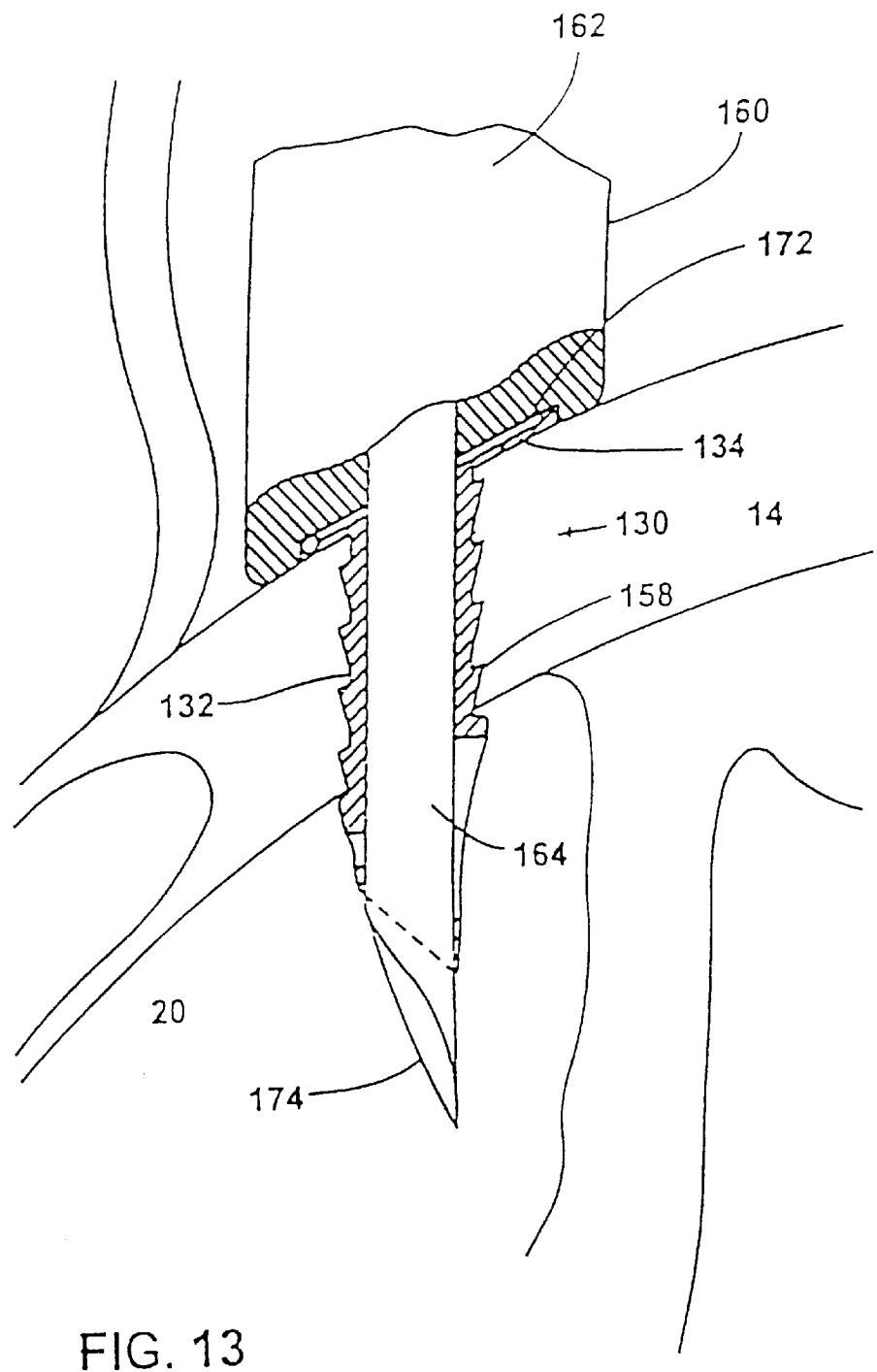
FIG. 13 illustrates a delivery device and insertion of the intraocular implant of FIG. 11 into an eyeball.

FIG. 13 illustrates a delivery device 160 and a method of inserting the intraocular implant 130 into an eyeball. The implant 130 is slidably fixed over a needle 164 of the delivery device 160, which, similar to a standard medical syringe, has needle 164 attached to a housing 162. The tip 174 of needle 164, which passes through the implant 130, is acutely angled so that the tip 174 is generally in line with the angle of the lower part of the implant 130.

A front surface of the delivery device 160 is formed as an abutment surface angled to match the angle of the disk 134 and further comprises an indent 172 to hold the implant 130 in place during implantation. The shape of the delivery device 160 and the angled surface of the disk 134 prevent the implant 130 from rotating during implantation.

Figure 14:
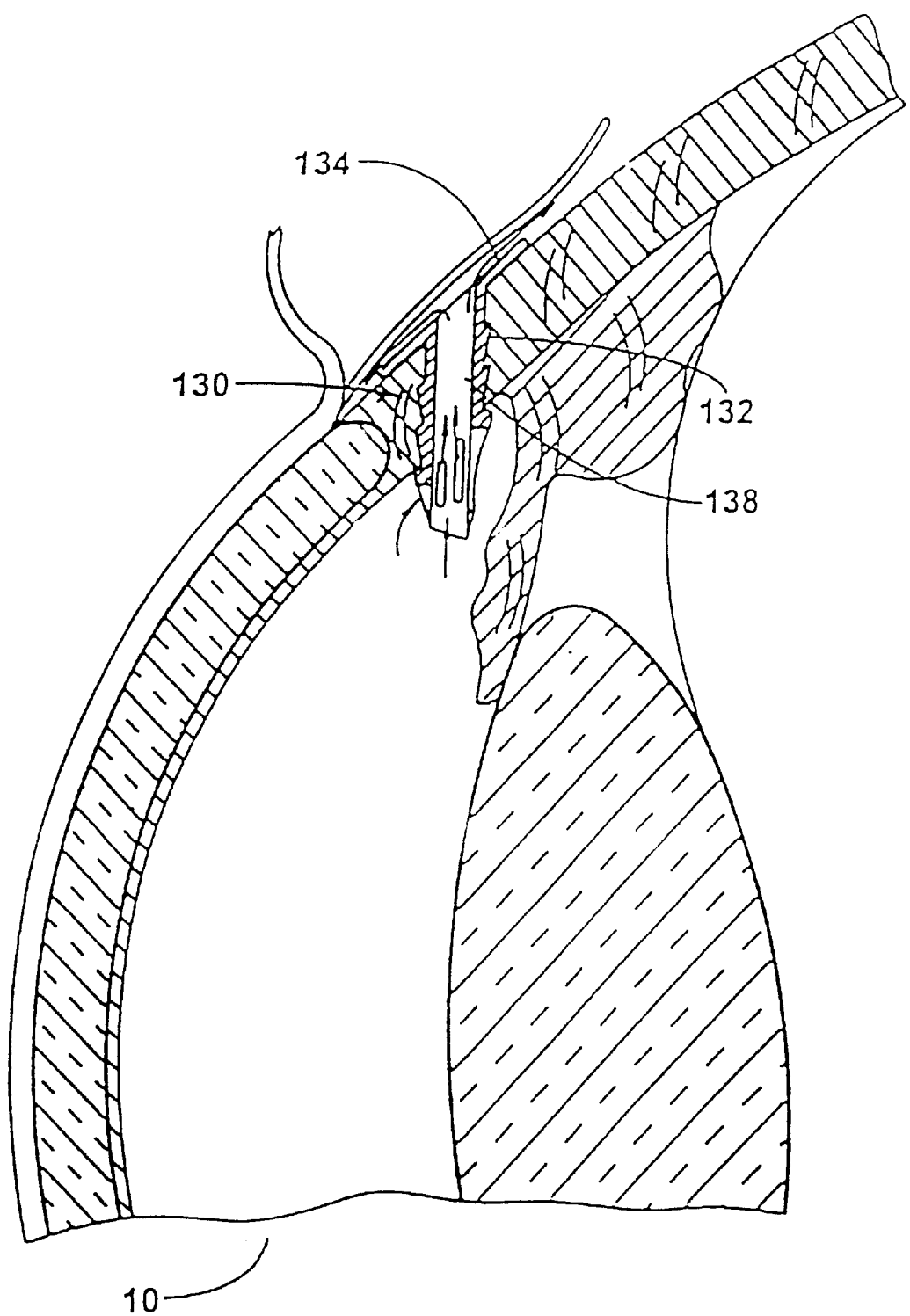
FIG. 14 is a schematic cross-sectional view of the intraocular implant of FIG. 11, shown inserted in an eyeball.

The delivery device 160 shown in FIG. 13 is used in a manner similar to that described above with reference to FIGS. 8 through 10. In this embodiment, however, the acute angle of the needle tip 174 pierces the sclera. The angled inlet end of the implant device 130 follows the needle tip 174 through the sclera 12, into the anterior chamber 20 of the eyeball. As shown in FIG. 14, the retention flanges 158 anchor the implant 130 in position and prevent the implant 130 from sliding out as the delivery device 160 is withdrawn. The anchorage of the retention flanges 158 also prevents the implant 130 from slipping out once in place.

FIGS. 15 and 16 illustrate a third embodiment of an intraocular implant. This embodiment is similar to that shown in FIGS. 1 through 10, with the exception that a separately attached retention projection in the form of a retention plate 252 is used for anchoring instead of the retention spur 52. The retention plate is inserted into a groove 253 in the tube of the implant 230 and may be fastened by any suitable means, for example by welding in the case of an implant 230 constructed of stainless steel.

An implant constructed in accordance with the invention may be manufactured entirely from or covered with any suitable material such as stainless steel, silicon, gold, nitinol, Teflon, tantalum, PMMA, or any other suitable plastic or other material. The implant may also be coated with heparin or any other suitable biologically active compound.

Manufacture of an implant in accordance with the invention may be carried out according to the following process. The tube may be formed from the tip of a standard stainless steel hypodermic needle. Using an EDM machine, small holes are drilled proximate the tip of the needle to form the circumferential holes. At a distance from the tip corresponding to the desired length of the tube, the needle is cut at the appropriate angle to correspond to the desired angle of the disk. The side of the needle is then undercut to form a projection which can be later bent outwardly to form the spur.

The disk may be chemically etched from a stainless steel sheet according to the following process. A pattern of the disk is drawn on a computer aided design (CAD) system and plotted on a transparent film using a laser plotter. Plottings are made of both the upper side and the lower side of the disk. The plotting for the upper side, for example, includes the outer rim and the inner uprights; the plotting for the lower side, for example, includes the base of the disk.

A layer of photoresist is adhered to both surfaces of the stainless steel sheet. The photoresist is then exposed to UV light through the film on which the plottings are made. The areas of the sheet which are blocked by the plottings are not exposed. The photoresist which has been exposed to UV light is then chemically removed.

Using an etching chemical, the stainless steel sheet is then etched, so that the chemical eats away the areas of the sheet from which the photoresist has been removed. The etching is time-controlled such that the chemical takes away material only to a predetermined depth.

By use of a plotting for the upper side which includes the outer rim and the uprights, the chemical on the upper surface of the sheet takes away material on the outside of the disk, in the reservoir including between the uprights, and in the center of the disk which is to receive the tube. Because the etching is time-controlled, the chemical acting on the top of the sheet takes away material only part way through the thickness of the sheet. By use of a plotting for the lower side which includes the base of the disk, the chemical on the lower surface of the sheet takes away material on the outside of the disk and in the center of the disk which is to receive the tube. The chemical acting on the bottom of the sheet takes away material part way through the thickness of the sheet. Because of action from both the top and the bottom, the material on the outside of the disk and in the center of the disk which is to receive the tube is completely taken away by the etching process through the entire thickness of the sheet. A small projection may be left on the outside of the disk during the etching process to prevent the disk from being dislodged from the sheet.

Figure 17:
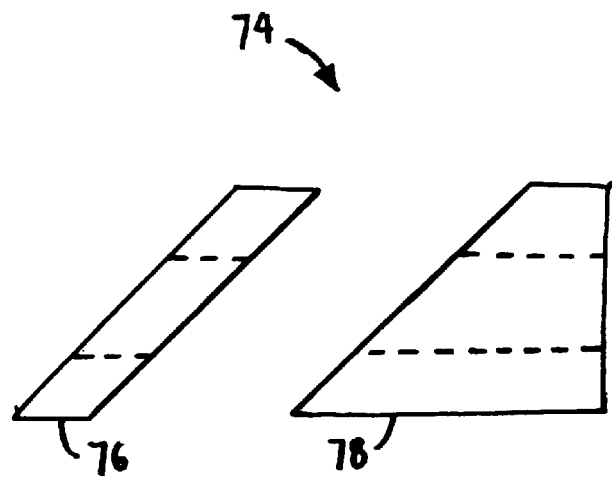
FIGS. 17 through 19 illustrate successive steps in a method of manufacturing an intraocular implant according to an embodiment of the invention, with FIG. 17 showing an outer tube cut in an initial phase of the manufacturing process, FIG. 18 showing the outer tube joined to an inner tube, and FIG. 19 showing the finished intraocular implant.
Figure 18:
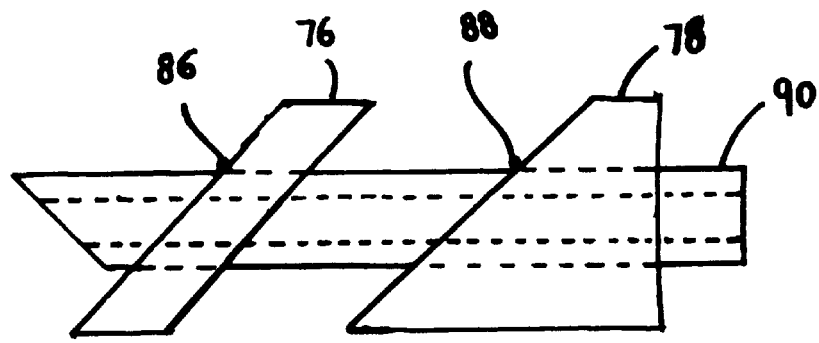
Figure 19:
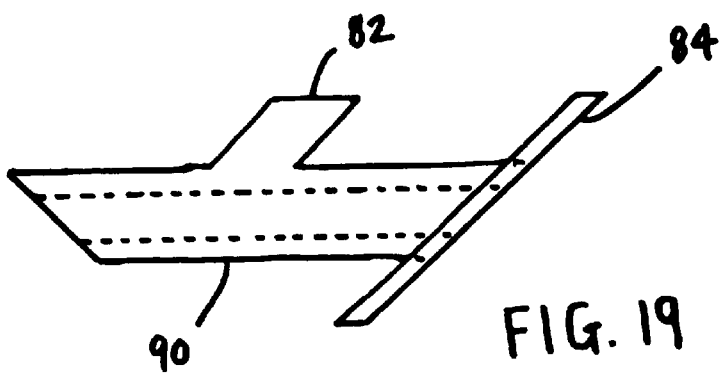

An alternative method for manufacturing an implant according to the invention is illustrated in FIGS. 17 through 19. FIG. 17 shows an initial step of the process in which an outer tube 74 having a longitudinal bore is cut into the illustrated pattern. The outer tube 74 may have, for example, an outer diameter of about 1 mm and an inner diameter (i.e., a diameter for its longitudinal bore) of about 400 micrometers. In the illustration, the outer tube 74 has been cut into two pieces 76 and 78; however, it should be recognized by persons skilled in the art that the two pieces 76 and 78 need not be completely separated. For example, the bottom half of the tube 74 could be left intact between the two pieces, leaving a connection piece in the form of a half-cylinder between the piece 76 and the piece 78.

In a next step of the process, illustrated in FIG. 18, a smaller inner tube 90 is placed inside the longitudinal bore of the remaining portion or portions of the outer tube 74. The inner tube 90 has an outer diameter that generally corresponds to the inner diameter of the outer tube 74. For example, the inner tube may have an outer diameter of about 400 micrometers. The inner tube also has a longitudinal bore, which may have a diameter, for example, of about 200 micrometers. When the inner tube 90 is placed inside the outer tube 74, the two tubes may be secured together, for example by welding the tubes together at the areas identified by reference numerals 86 and 88.

After the two tubes are joined together, further cuts are made to form the implant as shown in FIG. 19. This step includes simultaneously cutting the outer tube and inner tube along an angled plane at the outlet end of the implant to form the upper surface of the disk 84 and to cut away the unwanted portion of the inner tube 90 that would otherwise have projected beyond that upper surface of the disk 84. The portion of the inner tube 90 that remains after these final cuts forms the implant shaft. The portions of the outer tube 74 that remain after these final cuts form the retention projection 82 and the disk 84.

It will be appreciated by persons having ordinary skill in the art that variations on this manufacturing process and other manufacturing processes are possible. For example, an implant made of plastic may be manufactured by a suitable molding operation.

Various mechanisms may be used, if desired, for giving different flow characteristics to the implant. It may be desirable to use implants with different flow characteristics for different patients and/or to have an implant in which the flow characteristics may be changed after implantation in a particular patient.

Figure 20:
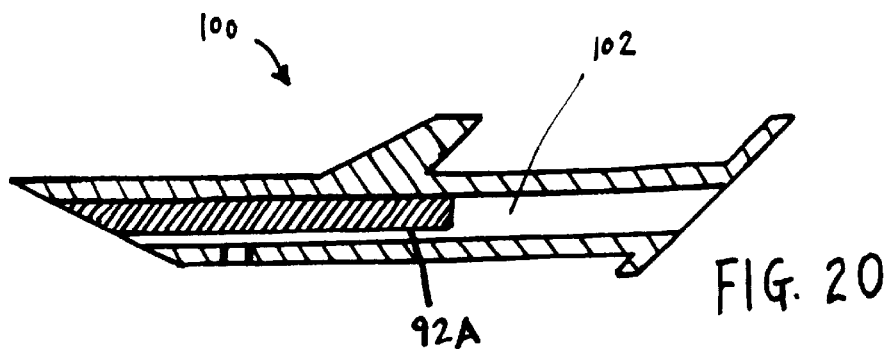
FIG. 20 illustrates an intraocular implant according to the invention with a flow controlling wire or rod in the tube passage.

FIGS. 20 through 25 illustrate various mechanisms for assisting in controlling the flow of fluid, e.g. aqueous humors, through an implant 100 according to the invention. In FIG. 20, the implant 100 has a flow controlling wire or rod 92A in the tube passage 102. The flow controlling rod 92A may be spot welded on one side to the inside of the tube passage 102.

The effect of the flow controlling rod 92A is to reduce the cross-sectional area through which the fluid flows for a particular length inside the tube passage 102 of the implant 100. Because the flow is a function of the cross-section and length of the lumen through which it passes, the interposition of the flow controlling rod 92A serves to increase the resistance to flow. In an intraocular implant, for example, this assists in reducing the risk of hypotony.

The diameter of the flow controlling rod 92A may be selected in accordance with the flow characteristics that are desired. For example, an internal tube passage of the implant having a diameter of 200 micrometers may be fitted with a flow controlling rod 92A having a diameter that is, for example, between 175 micrometers and 195 micrometers. A larger diameter for the flow controlling rod 92A provides more resistance to flow.

The length and cross-sectional shape of the flow controlling rod may similarly be selected to achieve the flow characteristics that are desired. FIGS. 21A through 21D show four possible cross-sectional shapes for the flow controlling rod. Flow controlling rod 92A has a circular cross-section. Flow controlling rod 92B is similar to flow controlling rod 92A with the addition of grooves 94B. Flow controlling rod 92C has a flat surface 96C. Flow controlling rod 92D has a longitudinal bore 98D.

Figure 22:
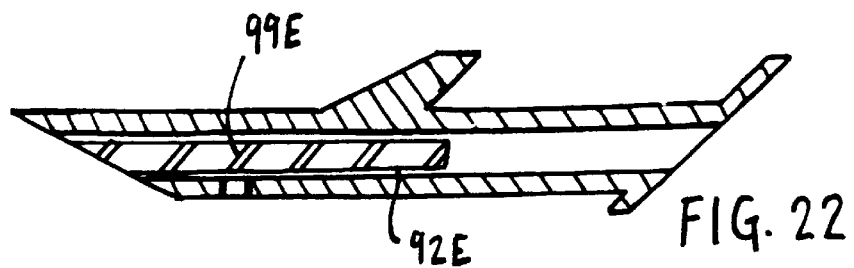
FIG. 22 illustrates an intraocular implant with a threaded flow controlling rod.
Figure 23:
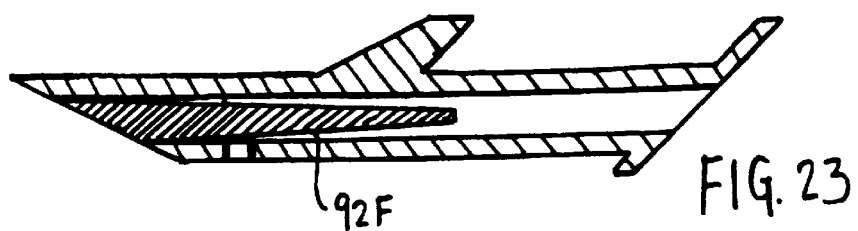
FIG. 23 illustrates an intraocular implant with a tapered flow controlling rod.
Figure 24:
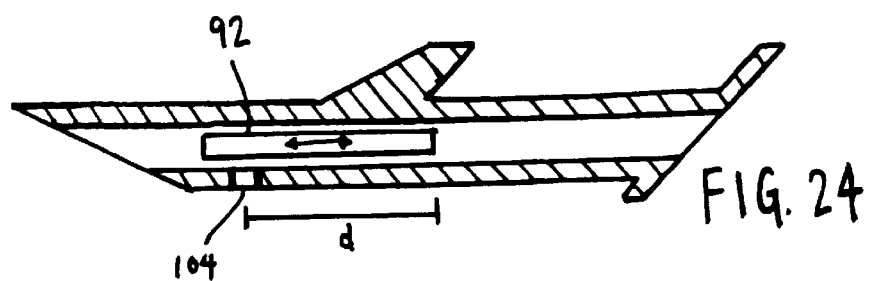
FIG. 24 illustrates an intraocular implant with an adjustable flow controlling rod.

FIGS. 22 and 23 illustrate further possible modifications to the flow controlling rod to modify the flow characteristics. As shown in FIG. 22, the flow controlling rod 92E may have an external helical groove 99E giving it a threaded appearance. If the diameter of the flow controlling rod 92E is large such that most or all of the flow occurs through the helical groove 99E, this embodiment provides a longer path for the fluid to travel and thus a greater resistance to flow. Additionally or alternatively, as shown in FIG. 23, the flow controlling rod 92F may be tapered or partially conical in shape. This embodiment provides less resistance to flow toward the outlet end of the implant. Persons skilled in the art will appreciate that numerous other variations are possible for the shape and size of the flow controlling rod.

Figure 21A:
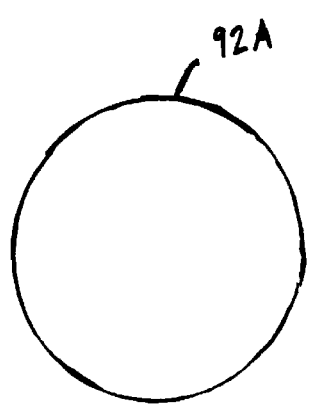
FIGS. 21A through 21D illustrate four variations of cross-sections for a flow controlling rod.
Figure 21B:
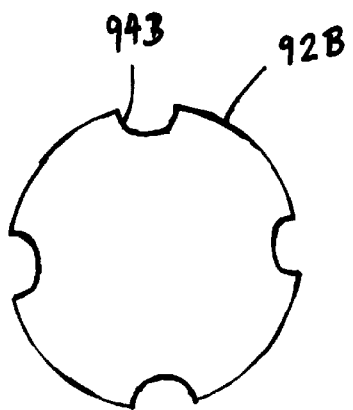
Figure 21C:
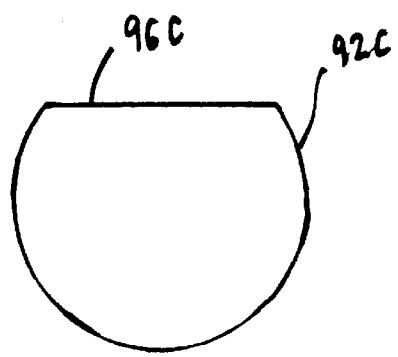
Figure 21D:
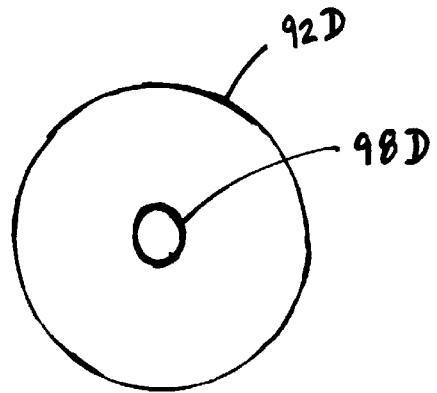

With the use of a flow controlling rod that is adjustable, the flow characteristics of the implant may similarly be adjustable. Thus, for example, the flow controlling rod may be mounted within the tube passage by only a friction fit, so that its position within the tube passage may be adjusted. As illustrated schematically in FIG. 24, the longitudinal position of the flow controlling rod 92 may be adjusted to provide a longer or shorter distance d for the fluid to travel from the inlet side hole(s) 104 to the end of the flow controlling rod 92. A longer distance d for the fluid to travel provides a higher resistance to flow. Another way to adjust the flow when using a flow controlling rod with a non-circular cross-section, as in FIGS. 21B and 21C, is to rotate the rod within the tube passage. This rotation changes the orientation of the rod with respect to the side holes 104, giving different flow characteristics to the implant.

The flow characteristics of the implant may be adjusted before implantation in accordance with the patient's needs, or, if desired, the implant may be constructed to allow for the flow characteristics through the implant to be varied after the implant has been implanted. After the implant has been implanted, the flow controlling rod 92 may be pushed forward toward the inlet end of the implant, for example by a tool with a wire. This reduces the distance d that the fluid must travel from the inlet side hole(s) 104 to the end of the flow controlling rod 92, and thus reduces the resistance to flow through the implant. Alternatively, a rod with a non-circular cross-section may be rotated after implantation.

Figure 25:
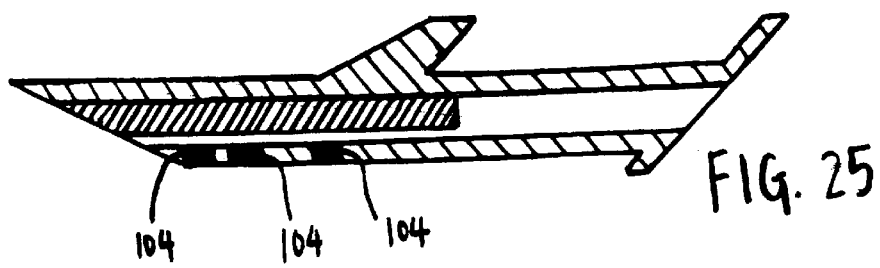
FIG. 25 illustrates an intraocular implant with selectively occluded side holes.

Another way to have different flow characteristics is to have different locations or configurations of the side holes 104. Thus, different models of the implant may have side holes in different locations and/or with different configurations. Alternatively, a single implant may have side holes which can be changed, for example by temporary occlusion of one or more of the side holes. FIG. 25 illustrates an implant with occluded side holes 104. The occlusion may be permanent or temporary. Temporary occlusion may be with an absorbable material or with a material that may be removed after implantation, for example by a tool or laser probe. In this way, the resistance to flow can be reduced after implantation.

Figure 26:
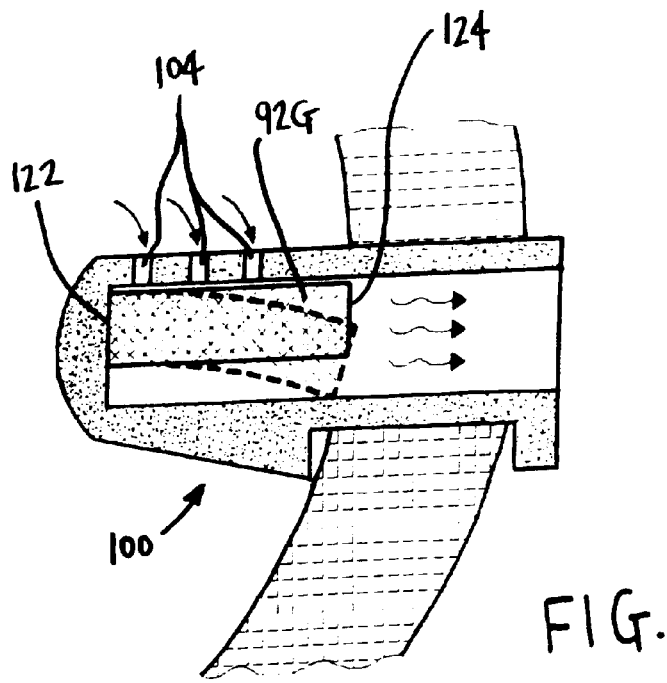
FIG. 26 illustrates an intraocular implant with a flexible flow controlling rod.

The implant may additionally or alternatively be designed to give different flow characteristics as a function of the fluid pressure. The flow controlling rod or wire may itself be flexible or movable and designed to flex or move in response to the fluid pressure. For example, as shown in FIG. 26, the flow controlling rod 92G may be fixed at one end 122 to a front end of the implant 100 with the other end 124 of the rod 92G unattached and free to bend. Before implantation, the rod 92G extends essentially parallel to the axis of the tube passage. When implanted, pressure from the fluid through the side holes 104 causes the rod 92G to flex, as indicated by the dashed lines. In this way, when the fluid pressure rises at the inlet end of the implant, the rod 92G bends to allow greater flow.

Figure 27:
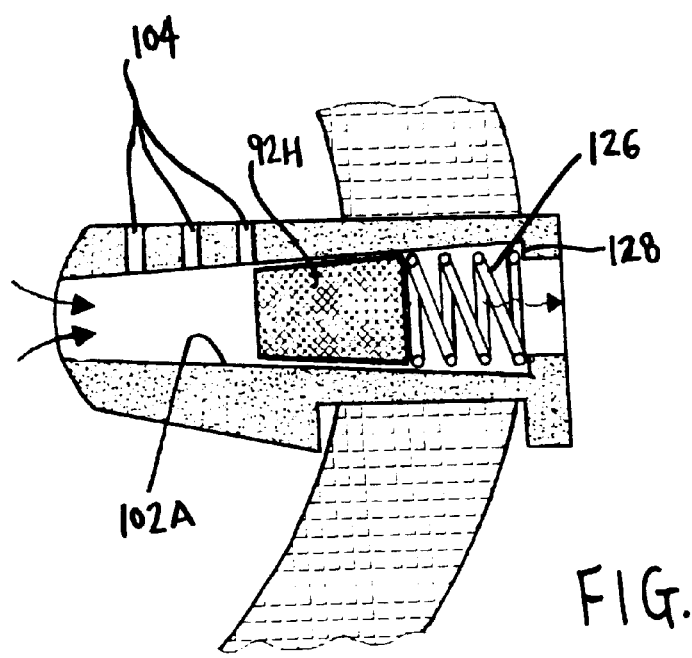
FIG. 27 illustrates an intraocular implant with a flow controlling rod biased against a spring.

Another related example is shown in FIG. 27. In that embodiment, the tube passage 102A is tapered and the flow controlling rod 92H is biased within the tube passage 102A by a spring 126. The flow controlling rod 92H is illustrated as tapered, but it will be appreciated that other shapes are possible. The spring 126 is shown as braced against a flange 128 near the outlet end of the tube passage 102A, but it will be appreciated that it also may be attached on the opposite side of the rod 92H near the inlet end of the tube passage 102A. When the fluid pressure increases at the inlet end, the force on the rod 92H causes the spring 126 to compress (or, if the spring is positioned on the opposite side of the rod, the force on the rod causes the spring to extend). The rod 92H is thus displaced longitudinally toward the outlet end of the implant, to a position at which the cross-section of the tube passage 102A is greater. Thus, the area through which fluid is allowed to flow is increased, allowing greater flow. As persons skilled in the art will appreciate, other variations are possible in which the rod moves or flexes to increase flow in response to increased pressure at the inlet end of the implant.

Figure 28:
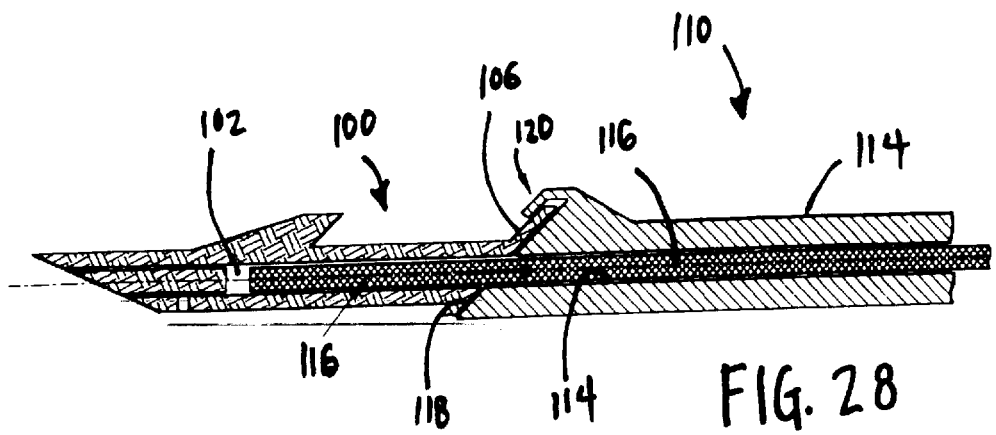
FIG. 28 illustrates the end of an embodiment of a delivery device according to the invention and an implant attached to the delivery device.

FIG. 28 illustrates an end portion of an alternative embodiment of a delivery deviced 110 according to the invention. The delivery device 110 has a handle (not shown) and a rodlike instrument 112. In this case, the rodlike instrument 112 has central bore 114 in which is located a retractable wire 116. The retractable wire 116 is positioned for penetrating a tube passage 102 of the implant 100 when the implant 100 is attached to the delivery device 110. The delivery device 110 has a retention mechanism including an abutment surface 118 having an angle generally corresponding to that of the disk 106 of the implant 100 for preventing the implant 100 from moving up the delivery device 110 during implantation and a hook 120 for preventing the implant 100 from moving down the wire 116.

For implantation, the implant 100 is placed over the wire 116 with the wire 116 projecting into the tube passage 102 and with the abutment surface 118 abutting against the disk 106 with the hook 120 retaining the disk 106 round the opposite side. FIG. 28 illustrates the end of the delivery device 110 in this condition, with the retention wire 116 in its forward position.

Figure 29:
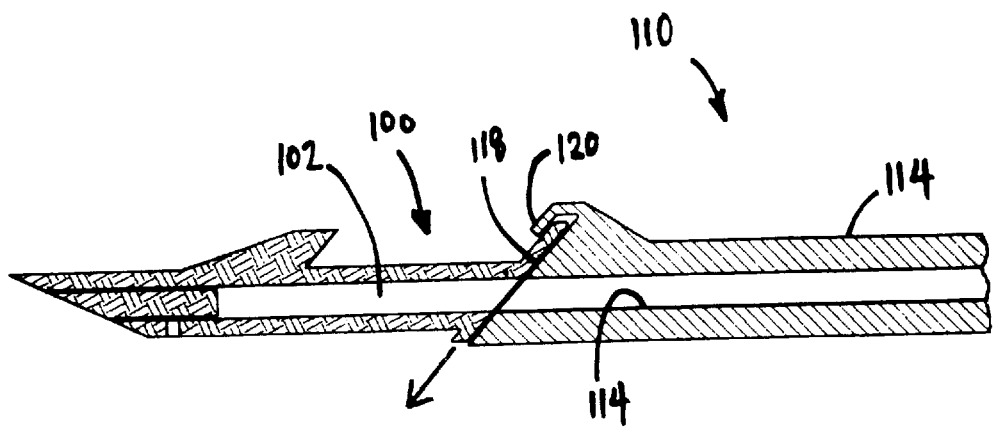
FIG. 29 illustrates a view similar to that of FIG. 28, with a retention wire of the delivery device retracted from the implant.

After the implant is in position, the retention wire 116 is retracted out of the implant 100. FIG. 29 illustrates the end of the delivery device 110 with the retention wire retracted. With the retention wire retracted, the implant is free to slide away from the hook 120, allowing the delivery device 110 to be withdrawn, leaving the implant in place.

As will also be appreciated by persons having ordinary skill in the art, the various embodiments of implants, methods of manufacture, delivery devices, and methods for implantation described hereinabove are given by way of example only. Various changes, modifications and variations may be applied to the described embodiments without departing from the scope of the invention, defined by the appended claims.

What is claimed is:

1. A method for manufacturing an implant comprising the steps of:
   selecting a first tube having a longitudinal bore and a second tube having a longitudinal bore and dimensioned to fit inside the longitudinal bore of the first tube;
   placing the second tube inside the longitudinal bore of the first tube; and
   cutting the first tube and the second tube to form the implant;
   wherein a portion of the second tube that remains after completion of the cutting forms an implant shaft having an inlet end and an outlet end and portions of the first tube that remain after completion of the cutting form a retention projection near the inlet end of the implant shaft and a flange of the implant near the outlet end of the implant shaft.

2. A method for manufacturing an implant as described in claim 1 wherein at least some of the cutting of the first tube is performed before the second tube is placed inside the longitudinal bore of the first tube.

3. A method for manufacturing an implant as described in claim 1 wherein at least some of the cutting of the first tube is performed after the second tube is placed inside the longitudinal bore of the first tube.

4. A method for manufacturing an implant as described in claim 3 wherein the cutting includes simultaneously cutting the first tube and second tube along an angled plane at the outlet end of the implant shaft.

5. A method for manufacturing an implant as described in claim 1 further comprising the step of welding the second tube to the first tube after the second cube is placed in the longitudinal bore of the first tube.

6. A method for manufacturing an implant as described in claim 1 wherein the flange near an outlet end of the implant shaft is a disk for resting on the sclera of an eye.

7. A method for manufacturing an implant comprising the steps of:
   selecting a first tube having a longitudinal bore and a second tube having a longitudinal bore and dimensioned to fit inside the longitudinal bore of the first tube;
   placing the second tube inside the longitudinal bore of the first tube; and
   cutting the first tube and the second tube to form the implant;
   wherein a portion of the second tube that remains after completion of the cutting forms an implant shaft having an inlet end and an outlet end and a portion of the first tube that remains after completion of the cutting forms a retention projection near the inlet end of the implant shaft.

8. A method for manufacturing an implant as described in claim 7 wherein at least some of the cutting of the first tube is performed before the second tube is placed inside the longitudinal bore of the first tube.

9. A method for manufacturing an implant as described in claim 7 wherein at least some of the cutting of the first tube is performed after the second tube is placed inside the longitudinal bore of the first tube.

10. A method for manufacturing an implant as described in claim 9 wherein the cutting includes simultaneously cutting the first tube and second tube along an angled plane at the outlet end of the implant shaft.

11. A method for manufacturing an implant as described in claim 7 further comprising the step of welding the second tube to the first tube after the second tube is placed in the longitudinal bore of the first tube.

12. A method for manufacturing an implant comprising the steps of:
   selecting a first tube having a longitudinal bore and a second tube having a longitudinal bore and dimensioned to fit inside the longitudinal bore of the first tube;
   placing the second tube inside the longitudinal bore of the first tube; and
   cutting the first tube and the second tube to form the implant;
   wherein a portion of the second tube that remains after completion of the cutting forms an implant shaft having an inlet end and an outlet end and a portion of the first tube that remains after completion of the cutting forms a flange of the implant near the outlet end of the implant shaft;

wherein the flange near an outlet end of the implant shaft is a disk for resting on the sclera of an eye.

13. A method for manufacturing an implant as described in claim 12 further comprising the step of welding the second tube to the first tube after the second tube is placed in the longitudinal bore of the first tube.

14. A method for manufacturing an implant as described in claim 12 wherein at least some of the cutting of the first tube is performed before the second tube is placed inside the longitudinal bore of the first tube.

15. A method for manufacturing an implant as described in claim 12 wherein at least some of the cutting of the first tube is performed after the second tube is placed inside the longitudinal bore of the first tube.

16. A method for manufacturing an implant as described in claim 15 wherein the cutting includes simultaneously cutting the first tube and second tube along an angled plane at the outlet end of the implant shaft.

* * * * *

UNITED STATES PATENT AND TRADEMARK OFFICE
CERTIFICATE OF CORRECTION

PATENT NO.    : 6,510,600 B2
DATED         : January 28, 2003
INVENTOR(S)   : Yaron et al.

It is certified that error appears in the above-identified patent and that said Letters Patent is hereby corrected as shown below:

<u>Column 14,</u>
Line 18, "cube" should read -- tube --.

Signed and Sealed this

Fifteenth Day of June, 2004

JON W. DUDAS
*Acting Director of the United States Patent and Trademark Office*